(12) United States Patent
Giudiceandrea et al.

(10) Patent No.: US 8,650,001 B2
(45) Date of Patent: Feb. 11, 2014

(54) METHOD FOR IDENTIFYING A PIECE OF WOOD AMONGST A PLURALITY OF STARTING PIECES OF WOOD AND/OR FOR DETERMINING ITS ROTATION WITH REFERENCE TO A KNOWN LAYOUT

(75) Inventors: Frederico Giudiceandrea, Bressanone (IT); Enrico Vicario, Mestre (IT)

(73) Assignee: Microtec S.R.L., Bressanone (IT)

( * ) Notice: Subject to any disclaimer, the term of this patent is extended or adjusted under 35 U.S.C. 154(b) by 303 days.

(21) Appl. No.: 13/185,784

(22) Filed: Jul. 19, 2011

(65) Prior Publication Data
US 2012/0022829 A1    Jan. 26, 2012

(30) Foreign Application Priority Data

Jul. 20, 2010   (IT) .............................. VR2010A0145

(51) Int. Cl.
*G06F 15/00*    (2006.01)

(52) U.S. Cl.
USPC ............... 702/167; 702/35; 702/40; 702/189; 250/559.25; 250/559.4; 378/58

(58) Field of Classification Search
USPC ................. 702/35, 40, 167, 189; 250/559.25, 250/559.4; 378/58
See application file for complete search history.

(56) References Cited

U.S. PATENT DOCUMENTS

| 5,023,805 A * | 6/1991 | Aune et al. ....................... 702/38 |
| 6,157,698 A * | 12/2000 | Pietikainen et al. ............ 378/58 |
| 2002/0168083 A1 | 11/2002 | Garms |

FOREIGN PATENT DOCUMENTS

| DE | 102004029252 A1 | 1/2006 |
| FR | 2797975 A1 | 3/2001 |
| WO | 2005010628 A1 | 2/2005 |

* cited by examiner

*Primary Examiner* — Jonathan C. Teixeira Moffat
*Assistant Examiner* — Hien Vo
(74) *Attorney, Agent, or Firm* — Pearne & Gordon LLP

(57) ABSTRACT

A method for identifying a piece of wood amongst a plurality or for determining its rotation includes the operating steps of: acquiring at least one piece of real X-ray information about the piece of wood; calculating, based on a tomographic reconstruction, a piece of virtual X-ray information in the same way as in the acquisition of the real X-ray information; comparing the real and virtual X-ray information to verify whether they match; and repeating the calculation and comparison steps up to obtaining the matching, and/or, for identification method only, selecting a different tomographic reconstruction and reiterating the calculation and comparison steps and, if necessary, the repetition and/or selection steps.

21 Claims, No Drawings

METHOD FOR IDENTIFYING A PIECE OF WOOD AMONGST A PLURALITY OF STARTING PIECES OF WOOD AND/OR FOR DETERMINING ITS ROTATION WITH REFERENCE TO A KNOWN LAYOUT

This invention relates to a method for identifying a piece of wood amongst a plurality of starting pieces of wood and/or for determining rotation of a piece of wood with reference to a known lay-out.

In particular, this invention was devised due to the need, acutely felt in the woodworking sector, to establish a correlation between a piece of wood during a predetermined examination/working step and the same piece of wood during other steps. In this context, the term piece of wood refers both to logs and to any products obtained from them (such as shorter pieces of logs, planks, etc.).

Obviously, the simplest method for obtaining said correlation is to carry out all of the various examinations and the various working operations one after another, gradually controlling the positioning of the piece of wood from start to finish.

However, said operating method cannot be followed in more modern plants where one or more working operations are often carried out on a group of pieces of wood, a group which is then transferred for one or more subsequent working operations and so on.

In particular, the wood may be cut even a relatively long time after the moment when it was examined. Consequently, since the method for cutting the wood as well as its subsequent intended use may depend on its physical features (presence or absence of knots, modulus of elasticity, etc.) it is essential to be able to access the information acquired during the examination both before and after cutting.

At present there are various wood traceability method which have been developed.

The simplest methods involve the application on the wood of a reference such as a text or bar code.

However, said methods did not prove very reliable both because after movement of the wood the reference may get dirty, come off or be erased, and because the wood may have a damaged surface which could invalidate the reading of a reference applied on it.

This Applicant provided a traceability method which uses the distinctive features of the surface of wood itself. In particular, said method involves preparing a three-dimensional reconstruction of the entire surface of the piece of wood for all of the pieces of wood in a certain group, acquiring a partial three-dimensional reconstruction of the surface of the piece of wood to be recognised and gradually comparing the partial reconstruction with the various overall reconstructions until superposable reconstructions are obtained.

Said method proved quite valid for logs which have sufficient surface features, but not as useful for logs whose surfaces are without distinctive elements or for planks which are all practically identical on the outside.

Moreover, none of the prior art methods described above allows recognition of the piece of wood from which a further piece of wood has been obtained by cutting.

In this context, the technical purpose which forms the basis of this invention is to provide a new method for identifying a piece of wood amongst a plurality of pieces of wood which overcomes the above-mentioned disadvantages.

In particular, the technical purpose of this invention is to provide a method for identifying a piece of wood amongst a plurality of starting pieces of wood which allows the identification both of a piece of wood in its entirety and of a part of it.

Another technical purpose of this invention is to provide a method for identifying a piece of wood amongst a plurality of starting pieces of wood which can also work for pieces of wood which are without significant surface three-dimensional distinctive features.

It is further technical purpose of this invention to provide a method for determining rotation of a piece of wood with reference to a known lay-out. In particular the method is of interest in the case where the piece of wood is a log or a piece of a log. Moreover, it is preferably of interest to provide a method which would allow to recognize rotation of a piece of wood with reference to a known starting condition, even after the piece of wood had undergone a variation of its water content (moisture).

The technical purpose specified and the aims indicated are substantially achieved by a method for identifying a piece of wood amongst a plurality of starting pieces of wood and by a method for determining the rotation of a piece of wood as described in the appended claims.

Further features and the advantages of this invention are more apparent in the detailed description, with reference to several preferred, non-limiting embodiments of a method for identifying a piece of wood amongst a plurality of starting pieces of wood and of a method for determining the rotation of a piece of wood.

For the purposes of this invention, the starting pieces of wood may be of any type. In particular, they may advantageously be logs or planks. Despite that, in the case of the method for determining rotation, they are preferably logs.

In the following the two methods will be described separately.

The method according to this invention, which allows the identification of a piece of wood amongst a plurality of starting pieces of wood, comprises as the initial step the preliminary acquisition of a tomographic reconstruction of each piece of wood in the plurality of pieces.

In particular, depending on the requirements and the ways of implementing the method, the step of preliminary acquisition of each tomographic reconstruction of the various starting pieces of wood may consist of detecting it using a tomograph, or simply retrieving reconstructions which were previously saved (if necessary, detected and saved even in locations other than that where the identification method is implemented). Once the tomographic reconstructions are available (obviously saved in a suitable computer), the method comprises taking a first piece of wood to be identified, which is known to belong to the plurality of starting pieces. That means that it may be a piece of wood which has remained the same compared with when the tomographic reconstructions were saved, or a piece of wood which only matches part of a starting piece of wood. In particular, when the starting piece of wood was a log, the first piece of wood may be the same log, it may be a shorter log obtained by dividing the starting log longitudinally into several parts, or it may be a plank obtained by cutting the starting log. The method then comprises acquiring at least one piece of real X-ray information about the first piece of wood to be identified.

The expression real X-ray information refers to any information about the internal structure of the first piece of wood obtained by means of an X-ray method. Therefore, in particular, the step of acquiring the real X-ray information may be carried out by taking a single X-ray of the first piece of wood, or by taking a plurality of X-rays of the first piece of wood according to a plurality of different directions of observation, or by performing a tomographic scan of the first piece of wood. In the first case the real X-ray information corresponds to the individual X-ray (which is in the form of a single one- or two-dimensional image), in the second case it is the set of X-rays acquired (each of which, in turn, is in the form of a single one- or two-dimensional image), whilst in the third case the real X-ray information corresponds to the result of the tomographic scan (which, like the above-mentioned tomographic reconstructions, is in the form of a three-dimensional virtual volume). Therefore, in the first two cases each piece of real X-ray information consists of a set of two-dimensional basic volumes (pixels) each representing the density integral of the first piece of wood in the direction of action of the X-ray. In contrast, in the third case each piece of real X-ray information consists of a set of three-dimensional basic volumes (voxels) each representing the real density of the first piece of wood in that position.

The real X-ray information acquired in this way is then used to establish a match between the first piece of wood and the tomographic reconstruction corresponding to it. To do that, the method comprises a substantially iterative approach, if necessary preceded by and/or supplemented with steps for reducing the number of iterations, as described in more detail below.

The starting point of the iteration is that of selecting a tomographic reconstruction of one of the starting pieces of wood or a part of it. Depending on the methods used to implement it, this step may be carried out in either a substantially random way, by arbitrarily selecting the tomographic reconstruction, or based on the information already available. In the latter case, in particular, the selection step comprises a preliminary step of checking the compatibility of the shape and/or dimensions and/or other known features of the tomographic reconstruction with the first piece of wood. For example, if the first piece of wood is a log, the length, diameter, curvature, taper, etc. may be compared. Alternatively, if the first piece of wood is a part of a starting piece of wood, and if the various cutting patterns used for each starting piece of wood are known, it is possible to select the tomographic reconstruction from those compatible with the first piece of wood in terms of shape and dimensions, thus greatly reducing the number of operations necessary to obtain the recognition.

Moreover, even more particularly, when the first piece of wood is a plank and the starting pieces of wood were logs, the step of selecting the tomographic reconstruction may comprise selection of a portion of one of the tomographic reconstructions corresponding to the starting logs, identified based on the possible cutting patterns used. In other words, the cut is made even virtually on the tomographic reconstructions. Once the tomographic reconstruction has been selected, the method comprises calculating a piece of virtual X-ray information based on that tomographic reconstruction. The expression virtual X-ray information refers to what could be obtained from the piece of wood or from the part of it to which the selected reconstruction refers if one were to act in the same way as was done for the first piece of wood to acquire the real X-ray information.

This means first, based on the tomographic reconstruction, virtually simulating performance of the same X-ray examination that was carried out on the first piece of wood. For example, in the three cases described above, it would mean simulating either a single X-ray or a plurality of X-rays according to different directions, or a tomographic scan.

If the real X-ray information consists of one or more X-rays, the step of calculating each piece of virtual X-ray information is carried out by simulating taking the same virtual X-rays on the respective tomographic reconstruction.

In particular, the step of calculating the virtual X-rays may comprise, for each X-ray, virtually positioning (by means of computer processing) a virtual source of X-rays and a virtual detection sensor relative to the selected tomographic reconstruction, with the same features and in the same relative position adopted by the real source of X-rays and detection sensor used for detecting the real X-ray information (this information being known). In this way, it is possible to calculate the virtual X-rays as virtual projections of the densities of the selected tomographic reconstruction on the virtual sensor in virtual directions of emission of the virtual source of X-rays.

It should be noticed that correct positioning of the virtual source and sensor is essential if the real X-rays were taken with a source of diverging X-rays. In fact, incorrect positioning would result in a distortion of the virtual X-ray information.

In contrast, if the real X-ray information consists of a tomographic reconstruction of the first piece of wood, the calculation of the virtual X-ray information is quite simple, since the calculation step may be carried out by simply making the virtual X-ray information match the selected tomographic reconstruction.

Once virtual X-ray information compatible with the real X-ray information has been obtained (by acquisition/calculation methods), the method according to this invention comprises comparing the real and virtual X-ray information obtained in this way to verify if they at least substantially match. In the above examples the comparison step is carried out by comparing the real and virtual X-rays/tomograms.

As already indicated, the real and virtual X-ray information all consist of at least one two- or three-dimensional grid of basic cells (pixels or voxels). Therefore, the comparison step comprises a cell-by-cell comparison of the grids.

The criteria for establishing whether or not the various information substantially matches may be established on each occasion by the technician depending on operating requirements. However, in the preferred embodiments, it is possible to foresee that the verification step will have a positive result when the difference between the grids is below a preset threshold value, both considering the grids as a whole (a solution allowing any localised acquisition or calculation errors to be ignored) and considering each individual cell.

In general, as already indicated, the method then comprises reiteration of the various steps.

This may be done either based on the same selected tomographic reconstruction, or based on a different tomographic reconstruction.

However, in the preferred embodiment the two possibilities are used one after another. Therefore, first the method comprises repetition of the calculation and comparison steps for a plurality of different pieces of virtual X-ray information obtainable, based on the same selected tomographic reconstruction mentioned, acting in the same way as for the acquisition of real X-ray information relating to the first piece of wood. Indeed, for a predetermined selected tomographic reconstruction, by rotating it relative to the virtual source of X-rays and sensor, it is possible to obtain different virtual X-ray information. Therefore, advantageously, with each reiteration the tomographic reconstruction is rotated (relative to the virtual source and sensor) through a predetermined angle (which may be several degrees or several tenths of a degree), preferably until a 360° rotation of the reconstruction has been covered.

Therefore, preferably, the method comprises, during the step of comparing the X-ray information, performing the comparison a plurality of times for a plurality of different reciprocal arrangements (mirroring or rotations) of the real and virtual X-ray information.

In particular, it is advantageous to turn upside down one of the two and repeat the comparison, since each piece of wood may be observed "the right way up" or "turned upside down" without distinction.

In the same way, two or more comparisons are also performed by translating the real and virtual X-ray information relative to each other.

As indicated, the other possibility allowed is that of selecting a different tomographic reconstruction available and reiterating the calculation and comparison steps and, if necessary, the repetition and/or selection steps.

However, in any case, the method finally comprises identification of the first piece of wood with a starting piece of wood corresponding to a selected tomographic reconstruction for which the verification step returned a positive result.

However, depending on the methods of implementation, even in this case there may be several possibilities.

The first possibility comprises identifying the first piece of wood with the starting piece of wood corresponding to the selected tomographic reconstruction for which the verification step returned a positive result for the first time. In other words, in this case the method stops the first time the verification step provides a positive result.

In contrast, a second possibility comprises identifying the first piece of wood with the starting piece of wood corresponding to the selected tomographic reconstruction for which the verification step had the best positive result, that is to say, for which the match between the virtual and real X-ray information is at the maximum amongst all of those available. Therefore, in this case, the method comprises performing all of the reiterations described above for each first piece of wood to be identified.

When the first piece of wood has been identified, the method is substantially finished at least in its most common embodiment.

In fact, in more complex embodiments, once the starting piece of wood corresponding to the first piece of wood has been identified, there may also be an operating step of identifying the position and/or orientation of the first piece of wood in space and/or relative to the selected tomographic reconstruction based on which the positive result was obtained.

Obviously, said step is more significant if the real X-ray information did not consist of a tomographic scan of the first piece of wood.

Knowledge of the position and orientation of the first piece of wood relative to the selected tomographic reconstruction (and therefore relative to the starting piece of wood to which it fully or partly corresponds) may be used both to carry out subsequent working (such as the cutting) in the best possible way, and to evaluate the internal properties of the first piece of wood (for example, in the case in which it is a plank obtained from a starting log).

Indeed, thanks to the method according to this invention, in the preferred embodiments its is sufficient to detect the tomographic reconstruction of a piece of wood once in order to retrieve as necessary not only that, but also its sub-parts corresponding to pieces of wood obtained by cutting.

Turning now to the method for determining rotation of a piece of wood, preferably a log, with reference to a known starting condition, it first comprises the operating step of preliminarily acquiring a tomographic reconstruction of the piece of wood. The tomographic reconstruction and its virtual orientation are assumed as the known starting condition with reference to which the rotation of the log must be determined (it is then a relative rotation).

In particular, depending on the requirements and the ways of implementing the method, the step of preliminary acquisition of the tomographic reconstruction of the piece of wood may consist of detecting it using a tomograph, or simply retrieving a reconstruction which was previously saved (if necessary, detected and saved even in locations other than that where the method of the present invention is implemented). In particular, tests executed by the applicant have shown that the present invention can be advantageously applied with excellent results even when, after acquisition of the tomographic reconstruction, the piece of wood has undergone variation of its water content (in particular it has dried).

Subsequently, when rotation of the piece of wood must be determined, the method of the present invention foresees to carry out a X-ray of the piece of wood to acquire at least a piece of real X-ray information about the piece of wood. The X-ray is carried out according to a real direction of observation, which is substantially orthogonal to a main direction of development of the piece of wood (that is to its longitudinal direction of development). It has to be noted that in the case of X-rays based on techniques as cone-beam (where rays are divergent) with direction of observation the direction passing through the center of the emitter is meant.

The method comprises then simulating (in the same manner as described with reference to the first method according to the present invention) the carrying out, on the tomographic reconstruction of the piece of wood, of a plurality of X-rays, by acting in the same way as was done to acquire the piece of real X-ray information, but according to a plurality of distinct virtual directions of observation substantially distributed around the piece of wood (or better, around its tomographic reconstruction).

In particular, virtual directions of observation, as the real one, are substantially orthogonal to the main direction of development of the piece of wood and are distributed around the tomographic reconstruction, advantageously uniformly, at known angles (for example, good results have been obtained with an angle of 20° between adjacent directions of observation). In this way, for each simulation, by means of the virtual X-ray a corresponding piece of virtual X-ray information is obtained.

At that point, the method comprises comparing the piece of real X-ray information with virtual ones, to identify a best virtual direction of observation for which the piece of virtual X-ray information is the most similar to the piece of real X-ray information. Advantageously, the similarity is evaluated on the basis of the difference between the two pieces of X-ray information either point-by-point (or better, cell-by-cell) or as a whole, according to the way above indicated with reference to the first disclosed method.

Finally, in general the method foresees to determine the rotation of the piece of wood with reference to the known starting condition, as a function of the orientation of the best virtual direction of observation with regard to the known starting condition.

In particular, the rotation of the piece of wood can be advantageously determined by making the real direction of observation coincide with the best virtual direction of observation and by evaluating the orientation of the best virtual direction of observation with reference to the known starting condition.

In turn, the best virtual direction of observation can either be chosen between the directions of observations for which the comparing step was performed (the one that gives the best results) or be calculated by processing of virtual directions of observation for which the comparing step was performed. In this second case, for example, you can use an interpolation function applied to the results of the comparing step (such as differences), and then calculate the virtual direction of observation corresponding to the minimum or maximum of that function.

However, in the most precise embodiments, it can also be foreseen that the correspondence, established between the real direction of observation and the virtual direction of observation, is considered as definitive only when the difference between the piece of real X-ray information and the corresponding piece of virtual X-ray information is less than a predetermined value.

Otherwise, in fact, the method advantageously foresees the repetition, eventually reiterated, of the steps of simulating and comparing, by locally increasing the resolution of analysis.

That means repeating such steps with reference to pieces of virtual X-ray information obtainable according to a plurality of further virtual direction of observation which are distributed, with known angular positions and greater resolution, around one or more directions of observation previously identified as the ones corresponding to the piece or pieces of virtual X-ray information most similar to the real one.

For example, if examination has been first carried out with directions of observation radially distributed one each 20° around the main direction of development, examination can be subsequently carried out with directions of observation distributed one each 4° around the direction/directions of observations which had given the best result.

Such a procedure can also be further reiterated depending on the wanted degree of precision (for example increasing resolution to 1° once identified the single or the best directions between the ones distanced of 4°).

Finally, it must be noted that, in other embodiments, it can also be foreseen to use, instead of one piece of real X-ray information, a plurality of pieces of real X-ray information obtained by X-rays executed according to a plurality of real directions of observation with a known reciprocal disposition. In that case, each processing based on the tomographic reconstruction shall be done by considering more directions of observation reciprocally disposed as the real ones.

This invention also brings important advantages.

First, the first method according to this invention allows the subsequent identification of both a piece of wood in its entirety and of a part of it.

Second, it can also work for pieces of wood which are without significant surface three-dimensional distinctive features, thanks to the fact that all of the pieces of wood always have very distinctive internal features.

Moreover, the second method according to the present invention allows to recognize rotation of a piece of wood, preferably a log, with reference to a known starting condition, piece of information which can be used for subsequent working of the piece of wood.

Finally, it should be noticed that this invention is relatively easy to produce and that even the cost linked to implementing the invention is not very high.

The invention described above may be modified and adapted in several ways without thereby departing from the scope of the inventive concept.

Moreover, all details of the invention may be substituted with other technically equivalent elements and the materials used, as well as the shapes and dimensions of the various components, may vary according to requirements.

The invention claimed is:

1. A method for identifying a piece of wood amongst a plurality of starting pieces of wood, characterised in that it comprises the operating steps of:
   preliminarily acquiring, through use of a machine, a tomographic reconstruction of each piece of wood of said plurality;
   taking a first piece of wood to be identified belonging to said plurality, there being the possibility that the first piece of wood is only part of a starting piece of wood;
   acquiring, through use of a machine, at least one piece of real X-ray information about the first piece of wood;
   selecting a tomographic reconstruction of one of the starting pieces of wood or a part of one of the starting pieces of wood;
   calculating, through use of a machine and based on the tomographic reconstruction, a piece of virtual X-ray information which could be obtained by acting on the piece of wood or on the part of piece of wood to which the reconstruction refers in the same way as was done for the first piece of wood to acquire the real X-ray information;
   comparing the real and virtual X-ray information obtained in this way to verify whether they at least substantially match; and
   repeating the calculation and comparison steps for a plurality of separate pieces of virtual X-ray information which can be obtained, based on the selected tomographic reconstruction, in the same way as for the first piece of wood for acquiring the real X-ray information; and/or
   selecting a different tomographic reconstruction available and reiterating the calculation and comparison steps and, if the verification step didn't return a positive result, the repetition and/or selection steps;
finally, the method comprising identification of the first piece of wood with a starting piece of wood corresponding to a selected tomographic reconstruction for which the verification step returned a positive result.

2. The method according to claim 1, characterised in that the identification step comprises identification of the first piece of wood with the starting piece of wood corresponding to the selected tomographic reconstruction for which the verification step returned the best positive result.

3. The method according to claim 1, characterised in that the identification step comprises identification of the first piece of wood with the starting piece of wood corresponding to the first selected tomographic reconstruction for which the verification step returned a positive result.

4. The method according to claim 1, characterised in that the step of acquiring real X-ray information comprises:
   taking a single X-ray of the first piece of wood, the real X-ray information corresponding to said single X-ray; or
   taking a plurality of X-rays of the first piece of wood in a plurality of different observations directions, the real X-ray information corresponding to the set of said X-rays;
also being characterised in that the step of calculating each piece of virtual X-ray information is carried out by simulating the taking of similar virtual X-rays on the relative tomographic reconstruction, and in that the comparison step is carried out by comparing the real X-rays with the virtual ones.

5. The method according to claim 4, characterised in that the step of calculating the virtual X-rays comprises, for each X-ray, positioning a virtual X-ray source and a virtual detection sensor, relative to the selected tomographic reconstruction, in the same relative position adopted by the real X-ray source and detection sensor used for detecting the real X-ray information, and calculating the virtual X-rays as projections of the densities of the selected tomographic reconstruction on the virtual sensor in virtual directions of emission of the virtual source of X-rays.

6. The method according to claim 1, characterised in that the step of acquiring real X-ray information comprises carrying out a tomographic scan of the first piece of wood, the real X-ray information corresponding to the result of the tomographic scan, and also being characterised in that the calculation step is carried out by making the virtual X-ray information coincide with the selected tomographic reconstruction.

7. The method according to claim 1, characterised in that the real and virtual X-ray information consist of at least one two-dimensional or three-dimensional grid of basic cells and also being characterised in that the comparison step comprises a cell by cell comparison between said grids.

8. The method according to claim 7, characterised in that the verification step returns a positive result when the difference between the grids, overall or in each cell, is below a preset threshold value.

9. The method according to claim 1, characterised in that the comparison step for the X-ray information comprises comparing a plurality of times for a plurality of different reciprocal arrangements the real X-ray information and the virtual X-ray information.

10. The method according to claim 1, characterised in that the step of preliminarily acquiring each tomographic reconstruction of the plurality of starting pieces of wood comprises either detecting it using a tomograph, or using a tomographic reconstruction previously saved.

11. The method according to claim 1, characterised in that the step of selecting a tomographic reconstruction of one of the starting pieces of wood or part of it comprises a preliminary step of checking the compatibility of size and/or shape and/or other known features of the tomographic reconstruction with the first piece of wood.

12. The method according to claim 1, further comprising, once a match with the first piece of wood has been identified, an operating step of identifying the position and/or orientation of the first piece of wood in space and/or relative to the selected tomographic reconstruction based on which the positive result was obtained.

13. The method according to claim 1, characterised in that the starting pieces of wood are logs, and the first piece of wood to be identified is a log or a plank.

14. The method according to claim 13, characterised in that when the first piece of wood is a plank, the step of selecting the tomographic reconstruction comprises selection of a portion of one of the tomographic reconstructions corresponding to the starting logs, identified based on the possible cutting patterns used.

15. A method for determining rotation of a piece of wood, such as a log, with reference to a known starting condition, comprising the operating steps of:
preliminarily acquiring, through use of a machine, a tomographic reconstruction of the piece of wood, the reconstruction defining the known starting condition;
subsequently carrying out, through use of a machine, a X-ray of the piece of wood according to a real direction of observation, substantially orthogonal to a main direction of development of the piece of wood, to thus acquire at least a piece of real X-ray information about the piece of wood;
simulating, through use of a machine, the carrying out, on the tomographic reconstruction of the piece of wood, of a plurality of X-rays, acting in the same way as was done to acquire the piece of real X-ray information, according to a plurality of virtual directions of observation substantially orthogonal to the main direction of development of the piece of wood and distributed around the tomographic reconstruction at known angles, to thus obtain a corresponding plurality of pieces of virtual X-ray information;
comparing the piece of real X-ray information and the pieces of virtual X-ray information;
on the basis of that comparison, identifying, with reference to the tomographic reconstruction, a best virtual direction of observation for which the piece of virtual X-ray information is the most similar to the piece of real X-ray information; and
determining the rotation of the piece of wood with reference to the known starting condition as a function of the orientation that the so identified best virtual direction of observation presents with regard to the known starting condition.

16. The method according to claim 15 further comprising, before the step of identifying the best virtual direction of observation, the repetition, eventually reiterated, of the steps of simulating and comparing, for pieces of virtual X-ray information obtainable according to a plurality of further virtual directions of observation distributed, with known angular positions and greater resolution, around one or more virtual directions of observation previously identified as the ones corresponding to the piece or pieces of virtual X-ray information most similar to the real one.

17. The method according to claim 15 wherein it is chosen as the best virtual direction of observation a virtual direction of observation for which the difference between the corresponding piece of virtual X-ray information and the piece of real X-ray information is less than a predetermined value, the rotation of the piece of wood being determined by making the real direction of observation coincide with that best virtual direction of observation.

18. Method according to claim 15, characterized in that the best direction of observation is either chosen between the directions of observations for which the comparing step was performed or is calculated by processing of virtual directions of observation for which the comparing step was performed.

19. The method according to claim 16 wherein it is chosen as the best virtual direction of observation a virtual direction of observation for which the difference between the corresponding piece of virtual X-ray information and the piece of real X-ray information is less than a predetermined value, the rotation of the piece of wood being determined by making the real direction of observation coincide with that best virtual direction of observation.

20. Method according to claim 16, characterized in that the best direction of observation is either chosen between the directions of observations for which the comparing step was performed or is calculated by processing of virtual directions of observation for which the comparing step was performed.

21. Method according to claim 17, characterized in that the best direction of observation is either chosen between the directions of observations for which the comparing step was performed or is calculated by processing of virtual directions of observation for which the comparing step was performed.

* * * * *